(12) United States Patent
Heresco-Levy

(10) Patent No.: US 9,687,460 B2
(45) Date of Patent: Jun. 27, 2017

(54) AUTOIMMUNE-INDUCED GLUTAMATERGIC RECEPTOR DYSFUNCTION METHODS AND TREATMENTS

(71) Applicant: SARAH HERZOG MEMORIAL HOSPITAL-EZRATH NASHIM, Jerusalem (IL)

(72) Inventor: Uriel Heresco-Levy, Jerusalem (IL)

(73) Assignee: SARAH HERZOG MEMORIAL HOSPITAL-EZRATH NASHIM, Jerusalem (IL)

( * ) Notice: Subject to any disclaimer, the term of this patent is extended or adjusted under 35 U.S.C. 154(b) by 0 days.

(21) Appl. No.: 14/893,992

(22) PCT Filed: May 26, 2014

(86) PCT No.: PCT/IL2014/050474
§ 371 (c)(1),
(2) Date: Nov. 25, 2015

(87) PCT Pub. No.: WO2014/191992
PCT Pub. Date: Dec. 4, 2014

(65) Prior Publication Data
US 2016/0120830 A1    May 5, 2016

Related U.S. Application Data

(60) Provisional application No. 61/827,764, filed on May 28, 2013.

(51) Int. Cl.
*A61K 31/198* (2006.01)
*A61K 45/06* (2006.01)
*A61K 31/496* (2006.01)

(52) U.S. Cl.
CPC .......... *A61K 31/198* (2013.01); *A61K 31/496* (2013.01); *A61K 45/06* (2013.01)

(58) Field of Classification Search
None
See application file for complete search history.

(56) References Cited

U.S. PATENT DOCUMENTS

2004/0157926 A1    8/2004  Heresco-Levy
2006/0167099 A1    7/2006  Biegon

FOREIGN PATENT DOCUMENTS

WO    WO2009018368    2/2009

OTHER PUBLICATIONS

Jan. 1, 2007, Dalmau, J. et. al., Paraneoplastic anti-N-methyl-Daspartate receptor encephalitis associated with ovarian teratoma, Annals of Neurology, John Wiley & Sons, Bostonn, US vol. 61, No. 1, Jan. 1, 2007, pp. 25-36, XP009122766, ISSN: 0364-5134, DOI: 10.1002/ANA.21050.
2011, Dalmau et al., "Clinical experience and laboratory investigations in patients with anti-NMDAR encephalitis", Lancet Neurol, vol. 10, 2011, pp. 63-74, XP027599021.
Nov. 2013, Nishikawa, Toru et. al., "[NMDA-type glutamate receptor and schizophrenia].", XP055134451Database Medline, US National Library of Medicine (NLM), Bethesda MD.
International Search Report issued in PCT/IL2014/050474 dated Aug. 25, 2014.
Jul. 24, 2010, Manto, M. et. al., "Afferent Facilitation of Corticomotor Responses is Increased by IgGs of patients with NMDA-receptor antibodies", Jul. 24, 2010., pp. 1-7, Springer-Verlag.
Nov. 26, 2010, Manto, M. et. al., "In vivo effects of antibodies from patients with anti-NMDA receptor encephalitis: further evidence of synaptic glutamatergic dysfunction",Nov. 26, 2010, Orphanet Journal of Rare Diseases., www.orjd.com/content/5/1/31.

*Primary Examiner* — Heidi Reese
(74) *Attorney, Agent, or Firm* — Neifeld IP Law, PC

(57) ABSTRACT

This invention provides a method of enhancing NMDAR-mediated neurotransmission in a disease associated with NMDAR antibody production, said method comprising administering an NMDAR agonist, an alanine-serine-cysteine transporter inhibitor, a D-amino acid oxidase inhibitor, a glycine transport inhibitor or a combination thereof to said subject. This invention also provides a method of mitigating the severity of, mitigating the pathogenesis of, lowering the incidence of or treating a disease associated with NMDAR antibody production, said method comprising administering an agent, which is an NMDAR agonist, an alanine-serine-cysteine transporter inhibitor, a D-amino acid oxidase inhibitor, a glycine transport inhibitor or a combination thereof to said subject.

11 Claims, 5 Drawing Sheets

AUTOIMMUNE-INDUCED GLUTAMATERGIC RECEPTOR DYSFUNCTION METHODS AND TREATMENTS

CROSS REFERENCE TO RELATED APPLICATIONS

This application is the U.S. national stage entry of PCT/IL2014/050474, filed May 26, 2014, which claims the benefit of U.S. Provisional Application No. 61/827,764, filed May 28, 2013; and these applications are both incorporated herein by reference.

BACKGROUND OF THE INVENTION

The present invention relates to pharmaceutical compositions for the treatment of autoimmune-induced glutamatergic receptor dysfunction and disorders related to same. More particularly, the present invention relates to the use of N-methyl-D-aspartate type glutamate receptor (NMDAR) agonists (NMDAR agonists, also known as NMDA agonists) and partial agonists for the treatment of autoimmune-induced glutamatergic receptor encephalitis.

NMDAR are a type of receptor for the excitatory neurotransmitter glutamate. NMDAR contain additional modulatory sites, including the following: glycine binding site, polyamine binding site, redox site, Zinc (Zn) site, phosphorylation sites, post-synaptic membrane docking sites and protein-protein interaction sites. The glycine binding site is sensitive to monocarboxyllic amino acids including the endogenous amino acids glycineD-serine and D-alanine. Glycine is synthesized via serine or threonine by serine hydroxymethyltransferase. Synaptic glycine concentrations are regulated by type 1 (GLYT1) and type 2 (GLYT2) glycine transporters, as well as by other amino acid transporters belonging to Systems A, L, ASC, and N.

GLYT1 transport inhibitors, such as N[3-(4'-fluorophenyl)-3-(4'-phenylphenoxy) propyl] sarcosine (NFPS), potentiate NMDAR activity in vivo, suggesting a critical role for glycine transporters in NMDAR regulation. Methylated glycine derivates (e.g., methylglycine, sarcosine) may serve as non-specific glycine transport inhibitors D-serine and D-alanine are metabolized by D-amino acid oxidase (DAAO), which is localized particularly in hindbrain. Further, DAAO is regulated by a novel protein termed G72, which may affect metabolic activity of the DAAO enzyme.

Glycine, D-serine and D-alanine levels in brain may be modulated by administering exogenous compound (i.e., glycine, D-serine or D-alanine), or naturally occurring precursors to these compounds including but not limited to L-serine, L-phosphoserine, D-phosphoserine and threonine, or by modulation of the synthetic enzymes serine hydroxymethyltransferase or serine racemase. D-Serine or D-alanine levels may also be increased by modulation inhibiting D-serine or D-alanine breakdown, for example, by antagonizing DAAO activity either directly or indirectly (e.g., via modulatory proteins).

Limbic encephalitis (LE) refers to an inflammatory process that predominantly affects the grey matter of the medial temporal lobes, amygdala and orbito-frontal cortex and produces cognitive impairment along with emotional and behavioral disturbances, sleep disruption, seizures and sometimes dementia. Until recently, autoimmune LE was mostly viewed as a paraneoplastic disorder associated with onconeural antibodies to intracellular antigens, cytotoxic T-cell mediated pathogenesis and limited response to treatment. However, accumulating data suggest that the clinical and immunological spectra of LE are far more extensive than initially considered. During the last decade a novel category of autoimmune encephalitides has emerged, that is characterized by antibodies against neuronal cell surface antigens, less frequent association with cancer, an antibody-mediated pathogenesis and improved treatment response following immunotherapy. Receptors and proteins that are critically involved in glutamatergic neurotransmission and synaptic plasticity, including N-methyl-D-aspartate and alpha-amino-3-hydroxy-5-methyl-4-isoxazol-propionic acid receptors (NMDAR, AMPAR) are cardinal target antigens in many of these disorders. Characteristic of these syndromes, the antibodies alter the structure and/or function of the corresponding neuronal antigen resulting in clinical pictures that resemble the pharmacological or genetic models in which the antigen is disrupted. Given the involvement of glutamatergic neurotransmission in a variety of psychiatric disorders, including schizophrenia and affective disorders, the identification of specific autoimmune-induced glutamatergic receptor dysfunctions (AGRD) is likely to have a substantial conceptual impact upon our understanding of neuropsychiatric disorders and to provide additional guidance for psychiatric diagnostics and treatments development.

NMDAR play a key role in the regulation of movement and striatal function and in the modulation of executive functions and effect. NMDARs are found on multiple classes of neuron within striatum including projection neurons and internuerons. NMDARs are composed of multiple subunits including an NR1 subunit which is present in virtually all functional NMDARs, and NR2 subunits that are present in variable proportions. Four NR2 subunits (NR2A-D) have been described. NR2A expression is high in GABAergic neurons that express the marker GAD67, intermediate over SP neurons, low in ENK neurons, not found in cholinergic and SOM neurons. In contrast, NR2B expression is intense in all populations of neurons, while expression of NR2C,D is weak The existence of multiple subforms of NMDAR in striatum is supported by the observation that NMDARs controlling GABA and DA release are less sensitive to NMDA than receptors controlling spermidine or ACh release.

Anti-NMDAR encephalitis is an autoimmune encephalitis characterized by the presence of antibodies against synaptic NMDAR. Anti-NMDAR encephalitis has become the most common and best characterized antibody-defined autoimmune neuronal disorder. Nevertheless, additional AGRD syndromes, associated with the presence of antibodies against diverse GLU neurotransmission-related antigens, including different NMDAR subunits, AMPAR and metabotropic receptor proteins are being increasingly characterized. Furthermore, the presence of NMDAR and AMPAR directed antibodies in conjunction with antibodies to different other types of receptors and neurotransmission systems has been reported. Overall, in view of the impact and interest generated by these findings, it is likely that during the next decade we will witness a significant expansion in the identification, characterization and understanding of AGRD.

The encephalitis associated with antibodies against NMDAR predominantly affects children and young adults, occurs with or without tumor association, responds to treatment but can relapse. The presence of a tumor (usually an ovarian teratoma) is dependent on age, sex and ethnicity, being more frequent in women older than 18 years and black women.

The exact incidence of anti-NMDAR encephalitis is unknown but it seems to be more frequent than any other known paraneoplastic encephalitis. Furthermore, due to the rareness of the syndrome and the varied clinical presentations ranging from psychiatric and neurological manifestations to autonomic dysregulation, the anti-NMDAR syndrome is still misdiagnosed and under-recognized.

Few laboratory diagnostic tests are available for anti-NMDAR encephalitis and related syndromes. The most accurate diagnostic finding is the presence of antibodies against NMDAR in the serum or CSF. Serum and CSF of patients suspected with the syndrome should be checked for reactivity with the hippocampal tissue on rat brain sections, cell-surface labeling of cultured hippocampal neurons, or reactivity with NR1/NR2 transfected human embryonic kidney (HEK) cells. The CSF may also present pleocytosis, increased protein concentration, oligoclonal bands and high IgG index. In vitro and in vivo studies demonstrate that patients antibodies decrease the surface density and synaptic localization of NMDAR clusters via antibody mediated capping and internalization, independent of the presence of complement, and without affecting other synaptic proteins, AMPARs or synapse density. The magnitude of these changes depends on antibody titer, and the effects are reversible when the antibody titer is reduced. Moreover, patients NR1 antibodies decrease NMDAR-, but not AMPAR-mediated synaptic currents.

This reversible NMDARs loss, and the resulting synaptic dysfunction, may underlie the deficits in memory, behavior and cognition that are hallmarks of anti-NMDAR encephalitis. Indeed, a remarkable feature of this disorder is the frequent reversibility of symptoms, even when these are severe and protracted. A decrease in serum antibody titers was demonstrated in parallel to immuno-modulatory treatment and clinical remission. Consequently, the effectiveness of therapeutic strategies may be assessed individually by quantitative determination of anti-NMDAR antibodies.

Other tests that can be done to support the diagnosis are electroencephalogram and MRI. Electroencephalogram can frequently demonstrate focal or diffuse slow activity during episodes of dyskinesias or abnormal movements and less commonly it may show epileptic activity. In many patients, MRI shows small areas of Fluid Attenuated Inversion Recovery (FLAIR) abnormalities in cerebral cortex outside the medial temporal lobes, sometimes involving the cerebellum and brainstem or transient enhancement of overlying meninges.

Immunotherapy and the detection and removal of a tumor (mostly teratoma) are the most important components in the treatment of anti-NMDAR encephalitis. Rosenfeld and Dalmau have proposed a structured treatment approach to patients with synaptic autoimmunities such as anti-NMDAR encephalitis. First, search for and remove a tumor. After tumor removal or if no tumor is found, 5-days course of concurrent IV Ig and methyl prednisolone should be given. If clear improvement is seen within 10 days, supportive care should be continued. If there is no response or limited response after one cycle of immunosuppression, cyclophosphamide (monthly) and rituximab (weekly for 4 weeks starting with the first dose of cyclophosphamide) should be initiated. For patients with limited or no response to these approaches, other forms of immunosuppression should be considered. For patients without tumors, immunosuppression with mycophenolate mofetil or azathioprine for at least one year after initial treatments should be considered, to reduce the high rate of relapses after recovery.

In patients without a tumor or with delayed diagnosis, additional treatment with second-line immunotherapy (rituximab or cyclophosphamide, or both) is usually needed with equivocal results. Relapses of anti-NMDAR encephalitis occur in 20% to 25% of treated patients, as well.

An accepted treatment of the syndrome is immunomodulation, which inadequately addresses the alleviation of psychiatric manifestations. There are several documented cases of neuroleptic administration actually exacerbating neuropsychiatric symptoms and movement abnormalities. ECT has been used for targeting catatonic presentations in patients with autoimmune encephalitis, including anti-NMDAR encephalitis. Agitated aggression has been treated with various conventional and atypical antipsychotics with limited treatment response. Atypical antipsychotics have also been used to target psychotic symptoms without significant success and have the potential to worsen dyskinesia and other movement abnormalities.

Thus there remains a need for the development of an appropriate therapeutic for encephalitis associated with antibodies against NMDAR, which is as yet lacking.

SUMMARY OF THE INVENTION

NMDAR agonist treatment significantly improves quality of life in subjects suffering from encephalitis associated with antibodies against NMDAR or other diseases whose pathogenesis is associated with the presence of antibodies against NMDAR, including reducing psychopathology symptoms, improving motor symptomatology and improving cognitive performance, including improving working memory, abstraction and mental flexibility.

This invention provides a method for enhancing NMDAR-mediated neurotransmission for encephalitis associated with antibodies against NMDAR or other diseases whose pathogenesis is associated with the presence of antibodies against NMDAR. In some embodiments, the invention contemplates use of glycine (GLY), D-Serine (DSR) or D-cycloserine (DCS), or combinations thereof, for their agonist activity for the NMDAR-associated GLY site in connection therewith. In some embodiments, the invention contemplates use of GLY transport inhibitors and D-amino acid oxidase inhibitors in connection therewith. In some embodiments the invention contemplates use of alanine-serine-cysteine transporter (ASCT) inhibitors and in some embodiments, the invention contemplates use of D-serine transporter inhibitors in connection therewith.

The present invention also provides for the use of an NMDAR agonist or partial agonist in the manufacture of a pharmaceutical composition, medical food, or dietary supplement for the treatment of encephalitis associated with antibodies against NMDAR or other diseases whose pathogenesis is associated with the presence of antibodies against NMDAR.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 1B shows the average spectra of EDB in the frontal region (F8 channel; thick line—average, thin line—SD) showing reduction in current latency post-treatment as compared to pre-treatment values (uV at 500 msec, lighter line), P=0.0083 t-test, two-tailed.

DETAILED DESCRIPTION OF THE INVENTION

Figures 1, 1A:
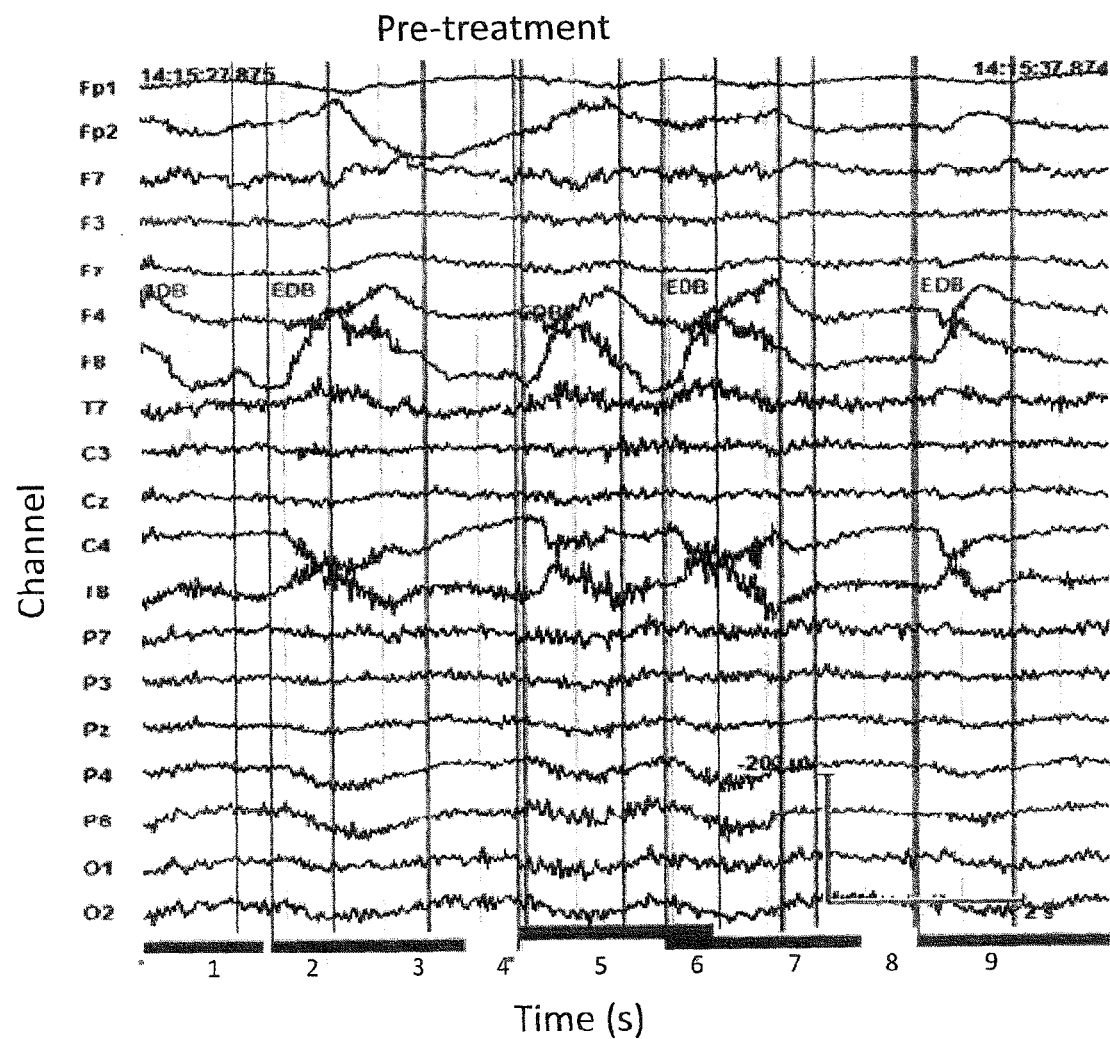
FIG. 1A and FIG. 1B demonstrate the reduction of an extreme delta brush (EDB) pattern after six weeks of D-Serine (DSR) therapy in a patient positive for the presence of anti-NR1 NMDAR antibodies. Pre- and Post-treatment effects are shown, as designated. Electroencephalogram (EEG) results with eyes opened are shown in FIG. 1A. Normal EEG background activity with superimposed semi-rhythmic diffuse delta frequency bursts more predominantly over the right frontal-temporal areas, characteristic of EDB is seen prior to treatment, that is significantly reduced post treatment.
Figures 1, 1A, 2:
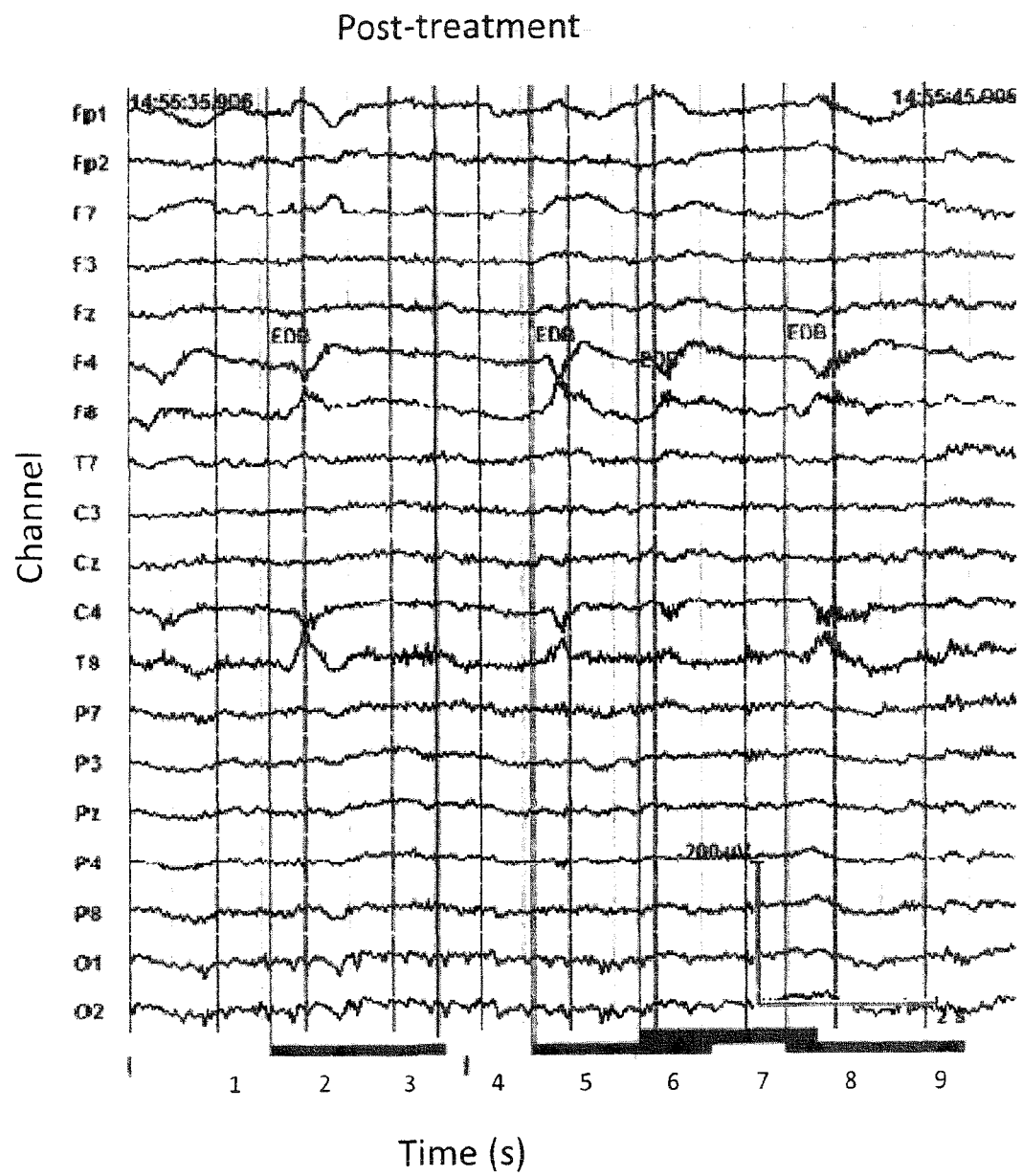

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

This invention provides a method of enhancing NMDAR-mediated neurotransmission in a disease associated with NMDAR antibody production, said method comprising administering an NMDAR agonist, an alanine-serine-cysteine transporter inhibitor, a D-amino acid oxidase inhibitor, a glycine transport inhibitor, a partial agonist such as D-cycloserine or a combination thereof to said subject.

This invention also provides a method of mitigating the severity of, mitigating the pathogenesis of, lowering the incidence of and/or treating a disease associated with NMDAR antibody production, said method comprising administering an agent, which is an NMDAR agonist, an alanine-serine-cysteine transporter inhibitor, a D-amino acid oxidase inhibitor, a glycine transport inhibitor, D-cycloserine or a combination thereof to said subject.

In some embodiments, the disease associated with NMDAR antibody production is paraneoplastic autoimmune encephalitis. In some embodiments, the disease associated with NMDAR antibody production is non-paraneoplastic autoimmune encephalitis. In some embodiments, the disease associated with NMDAR antibody production is anti-NMDAR encephalitis.

In some embodiments, the methods include identification of a subject with a disease associated with NMDAR antibody production. In some embodiments, according to this aspect, such methods include assessing qualitative or quantitative levels of NMDAR antibodies in a biological sample from a suspected subject. In some embodiments, the biological sample used in the methods described herein is a body fluid that is, in another embodiment, a cerebro-spinal fluid (CSF). In another embodiment, the body fluid is plasma. In another embodiment, the body fluid is any other type of fluid known in the art. Each possibility represents a separate embodiment of the present invention. In another embodiment, the biological sample is amniotic fluids, blood, sera, saliva, or their combination in another embodiment.

In some embodiments, the methods include identification of a subject with a disease associated with NMDAR antibody production by assessing other neurologic or psychiatric symptomatology. In one embodiment, encephalitis causes deficits that are characteristically dominated by rapid and severe loss of short-term memory. In another embodiment, patients show encephalitis with evidence of cancer.

In another embodiment, the encephalitis is associated with seizures. In another embodiment, the encephalitis is associated with a diencephalic syndrome. In another embodiment, the encephalitis is associated with a psychiatric symptom. In another embodiment, the encephalitis is associated with an abnormality in cognition. In another embodiment, the encephalitis is associated with an abnormality in behavior. In another embodiment, the encephalitis is associated with amnesia. In another embodiment, the encephalitis is associated with a memory deficit. In another embodiment, the encephalitis is associated with memory problems. In another embodiment, the encephalitis is associated with a hypokinetic syndrome.

In another embodiment, the encephalitis is associated with a movement disorder. In another embodiment, the encephalitis is associated with abnormal movements. In another embodiment, the movement disorder is Stiff Man/Person Syndrome. In another embodiment, the movement disorder is any other movement disorder known in the art. Each possibility represents a separate embodiment of the present invention.

In another embodiment, the encephalitis is associated with a decreased level of consciousness. In another embodiment, the encephalitis is associated with hypoventilation.

In another embodiment, the encephalitis is associated with, dysfunction of any part of the brain or spinal cord. In another embodiment, the encephalitis is associated with a combination of any of the above symptoms or disorders.

In another embodiment, the encephalitis is associated with a tumor. In another embodiment, the tumor is an ovarian teratoma. In another embodiment, the tumor is a thymic tumor. In another embodiment, the tumor is a testicular tumor. In another embodiment, the cancer associated with the encephalitis is a cervical cancer tumor. In another embodiment, the cancer is a head and neck cancer tumor. In another embodiment, the cancer is a breast cancer tumor. In another embodiment, the cancer is an ano-genital cancer tumor. In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is mesothelioma. In another embodiment, the cancer is a glioma. In another embodiment, the cancer is a germ cell tumor. In another embodiment, the cancer is a choriocarcinoma.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is nonsmall-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma.

In another embodiment, the tumor is any other type of tumor known in the art.

Methods for diagnosing encephalitis are well known in the art. In another embodiment, patients with encephalitis develop subacute confusion, irritability, depression, sleep disturbances, seizures, short-term memory loss, and/or dementia. In another embodiment, the pathological substrate of encephalitis is an inflammatory disorder that involves the limbic system (hippocampi, amygdala, and cingulate gyms). In another embodiment, biopsy and autopsy studies demonstrate interstitial and perivascular infiltrates of T cells, and less frequently B cells, along with microglial activation, neuronal degeneration, and/or gliosis. In another embodiment, inflammatory infiltrates are found in areas distant from the limbic system. In another embodiment, the infiltrates remain mild and clinically silent. In another embodiment, the infiltrates become prominent and develop into a disorder called encephalomyelitis. Additional methods of diagnosing encephalitis are described, for example, in Gultekin S H et al (Brain 2000; 123:1481-1494). Each possibility represents a separate embodiment of the present invention.

In some embodiments the method further comprises the step of removing the tumor, providing immunotherapy or a combination thereof.

Agents may be screened for effectiveness in stimulating NMDA transmission in vitro using assays, for example, measuring modulation of NMDAR-mediated activity in hippocampal slices or of NMDAR-stimulated dopamine release in isolated mouse striatum. Agents may be screened in vivo using assays, for example, measuring amphetamine induced dopamine release or NMDAR-mediated electrophysiological activity. Agents will be effective in ameliorating movement disorders at doses sufficient to potentiate NMDAR-mediated neurotransmission in vivo.

In addition to the embodiments listed above, prodrugs may also be administered. Prodrugs are defined as agents that are not themselves agonists of the NMDAR, but which enter the brain and are converted or metabolized there into effective agonists. An example of a glycine prodrug is milacemide. Simple precursors can be made by esterification, alkylation or other linkage, most effectively to hydrophobic groups that increase lipophilicity and diffusion into CNS.

In a preferred embodiment of the invention, NMDAR agonists, including but not limited to glycine, D-serine, or D-alanine, are conjugated to molecules that are actively transported into the CNS, leading to increased central penetration. Precursors to glycine, D-serine or D-alanine, including threonine, L-phosphoserine and D-phosphoserine, may also be incorporated into prodrugs.

In another aspect, the methods of the invention are useful in confirming suspected encephalitis associated with antibodies against NMDAR or other diseases whose pathogenesis is associated with the presence of antibodies against NMDAR, which method comprises confirming said encephalitis associated with antibodies against NMDAR or other diseases whose pathogenesis is associated with the presence of antibodies against NMDAR, as a result of a positive response by any of the indicia herein described, to treatment with an NMDAR agonist, an alanine-serine-cysteine transporter inhibitor, a D-amino acid oxidase inhibitor, a glycine transport inhibitor, a partial agonist such as D-cycloserine or a combination thereof.

The pharmaceutical compositions can be administered to the patient by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, or long term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid.

Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients.

For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

It will be apparent to those skilled in the art that various modifications and variations can be made in the solid substrates, kits, process and methods of the present invention without departing from the spirit or scope of the invention.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

In Vivo Efficacy of NMDAR Agonists in Anti-NMDAR Encephalitis

Anti-NMDAR encephalitis is diagnosed in a study subjects. Diagnosis is based on a determination of the presence of NR1 IgG antibodies in the serum/CSF of the subjects.

Patients of age 18-65, diagnosed with anti-NMDAR encephalitis on the basis of a) serum or cerebrospinal fluid (CSF) NMDAR antibody detection; and b) presentation of psychiatric and/or motor dysfunction symptoms will be assessed.

The patients will receive D-serine for 6 wks in addition to the clinically determined treatment.

Dosages of D-serine assessed will include staggered treatment regimens, including administration the first week of 1500 mg/d; and subsequent weeks, the subject will be administered a dosage of 4000 mg/d.

Changes in the assessed parameters over baseline will be recorded, including total scores of Positive and Negative Syndrome Scale and Abnormal Involuntary Movement Scale assessment, Continuous Performance Test, Verbal Memory Test, and Quality of Life Scale and others, as will be known to the skilled artisan.

Following the six week assessment period, subjects treated with D-serine will exhibit signs of improvement, as measured by significant score reduction in Positive and Negative Syndrome Scale and Abnormal Involuntary Movement Scale assessment, Continuous Performance Test, Verbal Memory Test, and Quality of Life Scale.

Example 2

Demonstration of Beneficial Effects of D-Serine in a Patient Positive for Anti-NR1 NMDAR Antibodies Materials and Methods Patient Inclusion and Exclusion Criteria The study was approved by the appropriate institutional review boards. Seventeen schizophrenia/schizoaffective patients fulfilled the inclusion criteria and were enrolled in the study. After complete description of the study, orally and in writing, informed consent was obtained from all participants. In order to be included in the study patients had to fulfill the following criteria:

1—Treatment-resistance to pharmacotherapy with presently available antipsychotic drugs and at least one of the following:
2—Abrupt start of disease, lack of patient/family history of psychiatric disorders and atypical disease course.
3—Presence or history of hebephrenic features
4—Presence or history of catatonic features
5—Presence or history of dyskinetic features and/or fulfillment of Schooler-Kane (1982) diagnostic criteria for tardive dyskinesia
6—Presence or history of seizure unaccounted by a neurological or other disorder.

Participants were excluded from participation in the study for any of the following reasons:
1) meeting criteria for DSM-IV Axis I diagnoses other than schizophrenia/schizoaffective disorder;
2) presence of a neurological disorder or history of significant head injury;
3) substance abuse or alcoholism during entire lifetime;
4) were judged clinically to be at suicidal or homicidal risk;
5) presence of an unstable and/or untreated medical disorder;
6) presence or history of renal dysfunction; and
7) female patients who were pregnant or lactating; female patients, if sexually active, had to be using medically accepted means of contraception.

Antibodies Assessment

A 5 cc. blood sample was obtained from each participating patient for the assessment of the presence of anti-NMDAR antibodies. Blood samples were prior to eating and prior to the administration of any type of medication.

Detection of autoantibodies against extracellular epitopes of NMDAR was performed in each of the serum samples obtained using a previously described cell-based assay (Takano et al., 2011 *Neurosci Res* 71:294-302). Patient serum samples were analyzed using cells expressing mutant NMDAR subunits by immunocytochemistry and on-cell Western analysis using live cells stably expressing mutant NMDAR. The presence of anti-NMDAR antibodies was evaluated using both X200 and X10 dilutions of the serum samples. Mutant GluRζ1(NR1, GluN1) subunits of NMDAR alone were expressed on the cell surface and direct evidence was obtained of the presence or absence of autoantibodies recognizing extracellular epitopes of GluRζ1 and the induction of internalization by autoantibodies in the serum of study patients.

D-Serine Clinical Trial

Out of the seventeen patients that entered the study, the serum of one patient was strongly positive at both serum sample dilutions for the presence of both IgG and IgM classes of anti-NR1 NMDAR antibodies. The patient was a 67 year old single female having a diagnosis of schizophrenia according to DSM-IV-R criteria (American Psychiatric Association, 2000 Diagnostic and Statistical Manual of Mental Disorders—(DSM-IV-TR), 4th edition. American Psychiatric Association Washington D.C. (Text Revision)). There was no history of mental disorder in the patient's family. The patient had completed post-high school studies and had worked as a secretary. At age 27, after a period of continuous headaches, for which no organic basis had been found, she had abruptly developed an acute psychosis characterized by grandiose and paranoid delusions, mystical thinking, elated affect and agitation. She had been hospitalized in a psychiatric hospital and underwent treatment with antipsychotic drugs and electroconvulsive therapy with only partial response. The patient had never returned to her previous functional level, and except for short attempts at living in the community, has been hospitalized ever since. She has been refractory to treatment with various classes of antipsychotic drugs, was not diagnosed with any medical or neurological disorder and was maintained on sulpiride 50 mg/day, citalopram 40 mg/day, lorazepam 1 mg/day and promethazine 50 mg/day.

Following the demonstration of anti-NMDAR antibodies, the patient was entered in an 8 week clinical trial with adjuvant DSR treatment. DSR is anaturally occurring amino acid that acts in vivo as an obligatoryco-agonist at the glycine modulatory site associated with NMDAR. No significant adverse events have been observed with DSR at doses of ≤4 g/day. Both acute and chronic administration of 1-2 g DSR in humans is known to result in ≥100 times increases in DSR serum levels (Kantrowitz et al., 2010, Schizophr Res 121:125-30; Heresco-Levy et al., 2005, Biol Psychiatry 57:577-85).

The trial consisted of two periods, starting with a 2 week lead-in/stabilization period (−2-0) following which the patient was entered in the second period of the study which consisted of a 6 week (0-6), open-label, fixed dose therapy phase. During this phase, the patient received adjuvant treatment with DSR, whose dose was increased from 1500 mg/day (week 1) to 2000 mg/day (weeks 2 and 3) to 3000 mg/day (weeks 4 and 5) and to 4000 mg/day (week 6). The doses of the ongoing medication received by the patient remained fixed throughout the study and no changes in medication were performed.

The patient underwent prior to entering the study and at study weeks 3 and 6 a medical work-up including complete medical history, and routine clinical blood work, including blood count+differential, lipids, and glucose levels, kidney, thyroid, and liver function parameters, urinalysis, and blood pressure measurements. Abdominal ultrasound was performed prior to study entry and electroencephalogram (EEG) and brain magnetic resonance imaging (MRI) were obtained pre- and post-DSR administration.

The assessment procedures used in the study included clinical and neurocognitive examinations. Motor and psychiatric symptoms as well as side-effects were rated biweekly throughout the study. The following instruments were used: 1) Positive and Negative Syndrome Scale (PANSS) (Kay et al., 1987, Positive and Negative Syndrome Scale (PANSS) rating manual. San Rafael Calif.: Social and Behavioral Sciences Documents); 2) Quality of Life Scale (QLS) (Wilkinson et al., 2000, Self-report quality of life measure for people with schizophrenia: the SQLS. Br J Psychiatry 177:42-6); 3) Abnormal Involuntary Movement Scale (AIMS) (Guy, 1976, ECDEU Assessment Manual for Psychopharmacology-Revised. Rockville, Md.: US Dept. of Health, Education and Welfare); 4) Simpson Angus Scale for Extrapyramidal Symptoms (SAS) (Simpson and Angus, 1970, Acta Psychiatr Scand Suppl. 212:11-9); and 5) Udvalg for Kliniske Undersøgelser (UKU) Side Effect Rating Scale (Lingjaerde, et al., 1987 Acta Psychiatr Scand Suppl 334: 1-100). In conjunction with UKU ratings, patient's vital signs and body weight were monitored throughout the study.

In addition, cognitive performance was assessed pre- and post-DSR treatment. For this purpose, a 1.5-hour neurocognitive assessment battery (nine computerized and two paper/pencil tests) was employed that measures accuracy and speed of performance in major cognition domains, including attention/vigilance, planning, short-term and working memory, decision making, abstraction and mental flexibility. All the tests were formatted like games and puzzles, and were administered to the patient as part of the comprehensive neuropsychiatric assessment at baseline and the end of study. The neurocognitive battery included the 1) Test of Attentional Vigilance (TOAV, (Forbes, 1998, Journal of Clinical Psychology 54:461-476; Greenberg, 1993, Journal of Child Psychology and Psychiatry 34: 1019-3)); 2) Tower of London (TOL, (Shallice, 1982, Specific impairments of planning. Philosophical Transactions of the Royal Society of London. Series B, Biological Sciences 298:199-209); 3-4) Digit Span Test (DST, forward and backward (Wechsler 1997, The Wechsler adult intelligence scale-III. San Antonio, Tex.: Psychological Corporation; Kaplan 1991, The WAIS-R as a neuropsychological instrument, San Antonio, Tex.: The Psychological Corporation; Lamar et al., 2007, Neuropsychologia 45:245-54; Lamar et al., 2008, Neuropsychologia 46:2597-601)); 5-6) Corsi Block Tapping Test (CBTT, forward and backward, (Corsi, 1972, Dissertation Abstracts International. 34:81913; Kessels et at, 2000, Applied Neuropsychology 7:252-58, Kessels et al., 2008, Assessment 15:426-34)); 7) Flanker Task (Erikson and Eriksen, 1974; Perception & Psychophysics 25: 249-63, Stins et, al., 2007, Advances in Cognitive Psychology 3:389-96); 8) Time Wall (Perez et al., 1987, Unified Tri-services cognitive performance assessment battery: review and methodology; DTIC Document ADA181697, and 9) Wisconsin Card Sort Test (WCST, (Berg, 1948, J Gen Psychol 39:15-22; Nelson, 1976, Cortex 12:313-24)). In addition to the nine computerized tests, the patient completed two paper/pencil tests: 10-11) part A and part B of the Trail-Making-Test (TMT, (Reitan, 1958, Percept. Mot Skills 8:271-76; Reitan, 1992 Trail Making Test: Manual for administration and scoring. Tucson, Ariz.: Reitan Neuropsychology Laboratory>> according to the guidelines presented by Spreen and Strauss (1998)). All neurocognitive testing was completed in a private and quiet setting to limit any distractions. The tests instructions were displayed and read to the patient by a Ph.D.-level trained researcher.

Results

Baseline medical and neurological examinations and clinical laboratory parameters of the patient were unremarkable with the exception of high prolactin and CMV IgG (76 U/mL) and EBV IgG (>750 U/mL) levels. Abdominal ultrasound examination showed no ovarian teratoma, which has been described among anti-NMDAR encephalitis patients (Dalmau et al., 2011, Clinical experience and laboratory investigations in patients with anti-NMDAR encephalitis. Lancet Neurol 10:63-74) or other space occupying lesions. The baseline EEG showed a normal EEG background activity with superimposed semi-rhythmic diffuse delta frequency bursts more predominant over the right fronto temporal areas (FIG. 1A, left). This type of pattern, denominated "extreme delta brush" (EDB) has been described in patients with NMDAR encephalitis and is consistent with the relative frontal and temporal glucose hypermetabolism described in some of these patients. Baseline brain MRI evidenced Fluid Attenuated Inversion Recovery (FLAIR) and T2 signal hyperintensities in the periventricular white matter, subcortically, and deep bifrontally and biparietally in the cortex. These type of findings have also been described in anti-NMDAR encephalitis. No hypophysis-related pathological findings were found.

DSR treatment was well tolerated throughout the study and no side effects were registered. As shown in Table 1, the quality of life of the patient improved considerably during treatment with DSR, resulting by the end of the treatment period in an ~3 times reduction in terms of reported symptoms and side effects. The patient entered the study having a relatively high PANSS total score of 97, including significant positive, negative, and general psychopathology symptoms. All these symptom domains improved during treatment with DSR and overall the total PANSS score registered by the end of the study was lower by 17%. Although motor symptomatology, as measured by AIMS and SAS scores, was minimal at baseline improvements were registered also in this domain following DSR administration (Table 1).

TABLE 1

Quality of life, psychiatric and motor symptoms of patient positive for anti NR1 NMDAR antibodies during 6 weeks treatment with D-serine.

| | | Study Week | | | |
|---|---|---|---|---|---|
| Outcome Measure | | 0 | 2 | 4 | 6 |
| QLS | Psychosocial | 60 | 55 | 50 | 38.33 |
| | Motivation/energy | 42.86 | 42.86 | 42.86 | 42.86 |
| | Symptoms/side-effects | 15.63 | 9.38 | 9.38 | 3.13 |
| PANSS | Positive | 24 | 21 | 21 | 19 |
| | Negative | 18 | 19 | 17 | 16 |
| | General | 55 | 54 | 51 | 45 |
| | Total | 97 | 96 | 89 | 80 |
| | AIMS | 1 | 0 | 0 | 0 |
| | SAS | 5 | 4 | 4 | 3 |

Abbreviations:
QLS, Quality of Life Scale;
PANSS, Positive and Negative Syndrome Scale;
CGI, Clinical Global Impression;
AIMS, Abnormal Involuntary Movement Scale;
SAS, Simpson Angus Scale for Extrapyramidal Symptoms.

The neurocognitive performance data of the patient pre- and post-DSR administration are shown in Table 2. Overall, DSR treatment had a favorable effect upon cognitive performance, as measured by the employed test battery, with evident improvements in the domains of working memory, abstraction and mental flexibility. While at baseline the patient could not comprehend/perform the DST, TMT and WCST tasks, these tests were successfully completed post-DSR treatment (Table 2).

TABLE 2

Neurocognitive performance of patient positive for anti NR1 NMDAR antibodies pre- and post-6 weeks treatment with D-serine

| | Neurocognitive Test | Pre-Treatment | Post-Treatment |
|---|---|---|---|
| TOAV | Omission errors | 1 | 2 |
| | Commission errors | 1 | 0 |
| | Response time, mean ± SD (milliseconds) | 562 ± 103 | 523 ± 93 |
| | TMT Part A (seconds) | 42 | 60.71 |
| ToL | ToL correctly solved trials, total (0-12) | 6 | 4 |
| | ToL preplanning time, mean ± SD (seconds) | 15.48 ± 4.43 | 11.24 ± 4.73 |
| | ToL movement execution time, mean ± SD, (seconds) | 22.57 ± 11.998 | 19.30 ± 15.42 |
| | ToL total time (0-720 seconds) | 456.582 | 366.415 |
| DST Forward | Span Length (3-9) | 6 | 7 |
| | Number Correct (0-14) | 8 | 9 |
| CBTT Forward | Span Length (2-9) | 5 | 4 |
| | Number Correct (0-16) | 8 | 6 |
| DST Backward | Span Length (3-9) | —* | 4 |
| | Number Correct (0-14) | —* | 3 |
| CBTT Backward | Span Length (2-9) | 4 | 3.5 |
| | Number Correct (0-16) | 6 | 5 |
| Flanker Task | Congruous response time, mean ± SD (milliseconds) | 725.03 ± 130.03 | 651.93 ± 130.16 |
| | Congruous accuracy, mean ± SD (proportion correct) | 0.475 ± 0.499 | 0.65 ± 0.476 |
| | Incongruous response time, mean ± SD (milliseconds) | 737.38 ± 131.34 | 713.3 ± 102.14 |
| | Incongruous accuracy, mean ± SD | 0.450 ± 0.499 | 0.575 ± 0.494 |

TABLE 2-continued

Neurocognitive performance of patient positive for anti NR1 NMDAR antibodies pre- and post-6 weeks treatment with D-serine

| | Neurocognitive Test | Pre-Treatment | Post-Treatment |
|---|---|---|---|
| | (proportion correct) | | |
| | Neutral response time, mean ± SD (milliseconds) | 732.18 ± 127.96 | 688.23 ± 99.19 |
| | Neutral accuracy, mean ± SD (proportion correct) | 0.475 ± 0.499 | 0.65 ± 0.476 |
| Time Wall | correctly estimated trials, total (0-20) | 12 | 6 |
| | accuracy score, mean ± SD | 0.056 ± 0.053 | 0.077 ± 0.051 |
| | TMT Part B (seconds) | 102 | 86.35 |
| WCST | Category Score | —* | 5 |
| | Trials to complete $1^{st}$ category | —* | 12 |
| | Total correct score % | —* | 81.25 |
| | Total error score % | —* | 18.75 |

Abbreviations:
TOAV, Test of Attentional Vigilance;
TMT, Trail-Making-Task;
ToL, Tower of London;
DST, Digit Span Test;
CBTT, Corsi Block Tapping Test;
WCST, Wisconsin Card Sorting Test.
—*, subject unable to complete task.

Figure 1B:
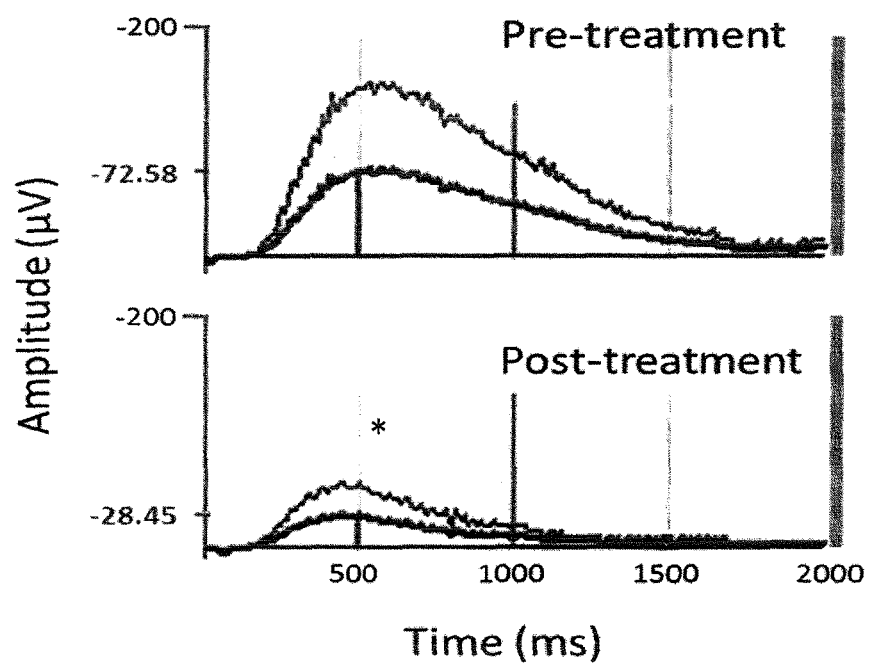
Figure 2A:
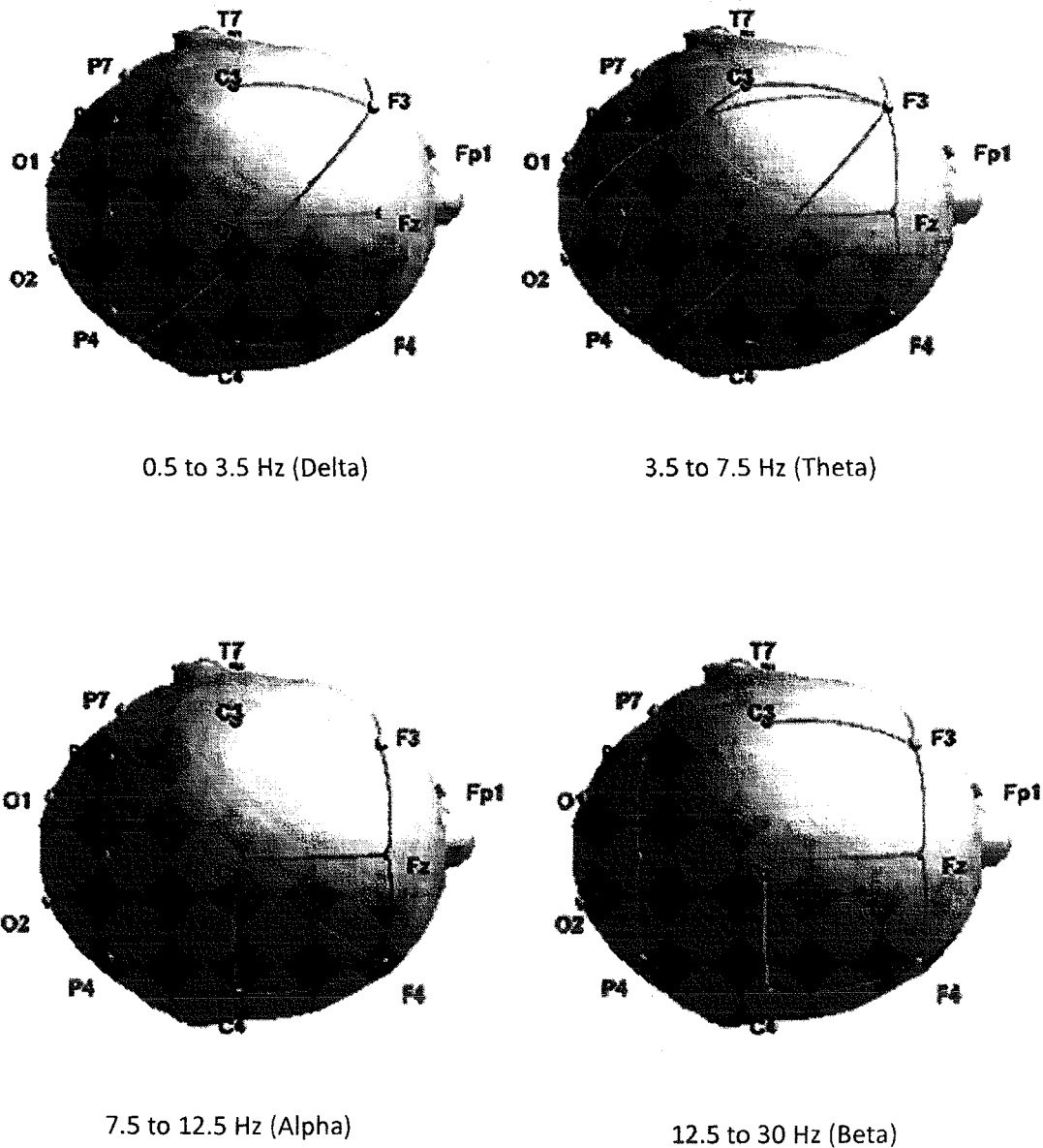
FIG. 2A and FIG. 2B show electroencephalogram (EEG) coherence values pre- and post-six weeks of D-serine administration in the same patient, respectively. Light gray lines indicate the amount of coherence between electrodes. Distinct new patterns of EEG coherence are present following DSR treatment, across all frequency bands. Channel abbreviations: frontal (Fz,F3,F4), central (Cz,C3,C4), temporal (T7), parietal (Pz,P7,P3,P4), occipital (O1,O2) brain regions.
Figure 2B:
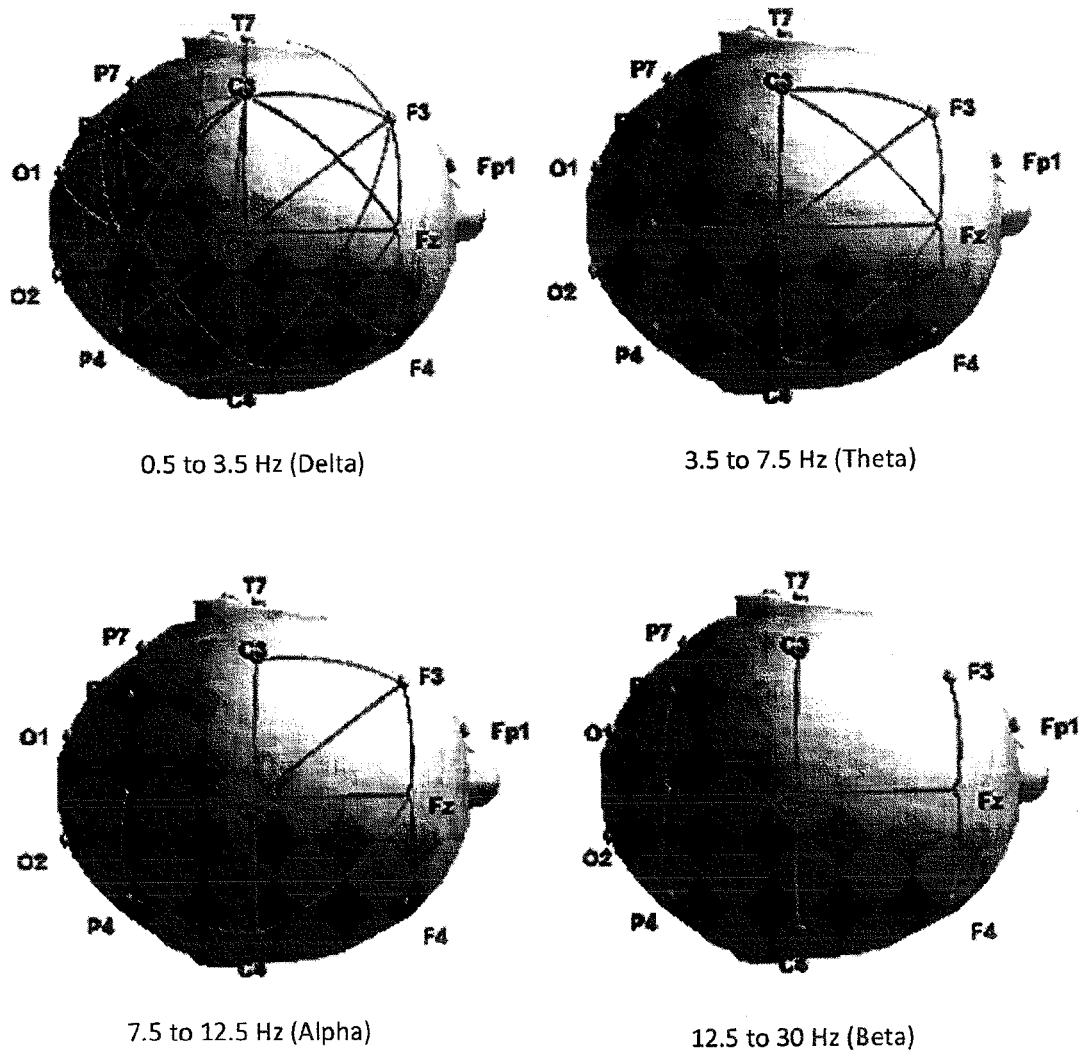

A response to DSR treatment, consisting of an attenuation of the EDB pattern, was also registered in terms of the EEG parameters registered pre- and post-DSR administration (FIG. 1A). A significant reduction in current latency of EDB over the right frontal area was registered following DSR treatment (t=2.686, df=113, p=0.0083, 95% confidence interval) (FIG. 1B).

Remarkably, short-term DSR treatment resulted in significantly improved quality of life, including reduction in psychopathology symptoms, improved motor symptomatology, improved cognitive performance, including improved working memory, abstraction and mental flexibility.

Example 3

In Vitro Efficacy of NMDAR Agonists in Anti-NMDAR Encephalitis

Rodent neuron cell cultures are treated with anti-NMDAR antibodies as described in Hughes E G et al., J Neurosci 2012 30(17):5866-75. D-Serine, for example at a concentration of 50-200 uM, or Glycine, at a concentration of 100-500 uM is added to some of the cultures, reversing receptor intracellular localization. The determination of receptors localization and other relevant measures is based on histological measurements.

Immunohistochemical methods will be applied to document (a) localization of NMDAR and NR1 and NR2 subunits; (b) loss of oligodendrocytes; (c) changes in astrocytes (S100beta) and microglia (cd11b), (d) expression of neurotrophic factors: brain derived neurotrophic factor (BDNF), nerve growth factor (NGF) and ciliary neurotrophic factor (CNTF); (e) markers of neurogenesis—doublecortin (17) and apoptosis—caspase3 (9). Quantification of histological measurements is based on images in several cortical subregions, striatum, globus pallidus, substantia nigra, hippocampus, and cerebellum.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A method for treating anti-NMDAR encephalitis, comprising:
   administering to a patient having an autoimmune encephalitis associated with antibodies against synaptic N-methyl-D-aspartate receptor (NMDAR), a therapeutically effective amount of D-serine.

2. The method of claim 1, wherein said encephalitis is associated with occult tumor.

3. The method of claim 2, wherein said tumor is an ovarian teratoma.

4. The method of claim 2, wherein said method further comprises the step Of removing said tumor, providing immunotherapy or a combination thereof.

5. The method of claim 1, further comprising administration of glycine (GLY), additional D-serine, D-cycloserine (DSR), or a combination thereof.

6. The method of claim 1, wherein D-serine is administered at a dosage of 30-60 mg/kg/d.

7. The method of claim 5, wherein glycine is administered at a dosage of 40-60 g/d.

8. The method of claim 5, wherein D-cycloserine is administered at a dosage of 250-1000 mg/d.

9. The method of claim 1, which is utilized during an acute stage of a disease associated with NMDAR antibody production.

10. The method of claim 1, which is utilized during a rehabilitational stage of a disease associated with NMDAR antibody production.

11. The method of claim 1, further comprising administration of an agent selected from the group consisting of alanine-serine-cysteine transporter inhibitor, a D-amino acid oxidase inhibitor, a glycine transport inhibitor or a combination thereof.

* * * * *